United States Patent
Lin et al.

(10) Patent No.: US 8,956,871 B2
(45) Date of Patent: Feb. 17, 2015

(54) CELL CULTURE SYSTEM AND SERUM-FREE METHOD FOR CULTIVATING CELLS

(71) Applicant: Industrial Technology Research Institute, Hsinchu (TW)

(72) Inventors: Pei-Ju Lin, Hsinchu (TW); Guilhem Tourniaire, Chilworth (GB); Yi-Chen Chen, Hsinchu (TW); Kathryn Swindells, Chilworth (GB); Bin-Ru She, Qionglin Township (TW); Hsiang-Chun Hsu, Taipei (TW); Chih-Ching Liao, Xinpu Township (TW); Su-Yo Lin, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 70 days.

(21) Appl. No.: 13/713,327

(22) Filed: Dec. 13, 2012

(65) Prior Publication Data
US 2014/0134734 A1    May 15, 2014

(30) Foreign Application Priority Data

Nov. 12, 2012 (TW) .............................. 101141978 A (51) Int. Cl.
*C12N 5/00* (2006.01)
*C12N 5/0775* (2010.01)
*C12N 5/07* (2010.01)
*C08F 220/14* (2006.01)
*C08F 220/18* (2006.01)
*C08F 220/28* (2006.01)
*C08F 222/26* (2006.01)
*C08F 220/06* (2006.01)

(52) U.S. Cl.
CPC ............ *C12N 5/0031* (2013.01); *C08F 220/14* (2013.01); *C08F 220/18* (2013.01); *C08F 220/28* (2013.01); *C08F 222/26* (2013.01); *C12N 5/0068* (2013.01); *C08F 220/06* (2013.01); *C12N 2533/30* (2013.01)
USPC ....................................................... 435/402

(58) Field of Classification Search
USPC ....................................................... 435/402
See application file for complete search history.

(56) References Cited

U.S. PATENT DOCUMENTS

| | | | |
|---|---|---|---|
| 6,583,228 B2 | 6/2003 | Nkansah et al. | |
| 6,905,875 B2 | 6/2005 | Yu et al. | |
| 7,736,689 B2 | 6/2010 | Chappa et al. | |
| 8,039,524 B2 | 10/2011 | Chappa et al. | |
| 8,168,433 B2 * | 5/2012 | Gehman et al. | 435/402 |
| 2002/0161156 A1 | 10/2002 | Nkansah et al. | |
| 2003/0165613 A1 | 9/2003 | Chappa et al. | |
| 2004/0023370 A1 | 2/2004 | Yu et al. | |
| 2005/0220891 A1 | 10/2005 | Yu et al. | |
| 2006/0019361 A1 | 1/2006 | Ng et al. | |
| 2006/0019362 A1 | 1/2006 | Yu et al. | |
| 2007/0292596 A1 | 12/2007 | Chappa et al. | |
| 2009/0191627 A1 | 7/2009 | Fadeev et al. | |
| 2009/0191632 A1 | 7/2009 | Fadeev et al. | |
| 2009/0203065 A1 | 8/2009 | Gehman et al. | |
| 2009/0286278 A1 | 11/2009 | Yu et al. | |
| 2010/0093093 A1 | 4/2010 | Leong et al. | |
| 2010/0099160 A1 | 4/2010 | Jiang et al. | |
| 2010/0240789 A1 | 9/2010 | Chappa et al. | |

(Continued)

FOREIGN PATENT DOCUMENTS

| | | |
|---|---|---|
| EP | 0 894 102 B8 | 1/2006 |
| EP | 2 292 691 A1 | 3/2011 |

(Continued)

OTHER PUBLICATIONS

Lydon et al., Cellular interactions with synthetic polymer surfaces in culture. Biomaterials, vol. 6 (Nov. 1985) pp. 396-402.*

(Continued)

*Primary Examiner* — Jon P Weber
*Assistant Examiner* — Kara Johnson
(74) *Attorney, Agent, or Firm* — Birch, Stewart, Kolasch & Birch, LLP.

(57) ABSTRACT

The disclosure provides a cell culture system and a serum-free method for cultivating cells. The cell culture system includes a substratum, wherein the substratum has a surface. A polymer is disposed on the surface of the substratum, wherein the polymer is prepared by polymerizing a first monomer with a second monomer. The first monomer has a structure as represented by Formula (I), and the second monomer has a structure as represented by Formula (II):

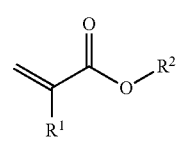

Formula (I)

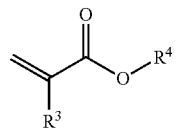

Formula (II)

wherein, $R^1$ is hydrogen or methyl; $R^2$ is methyl, ethyl, or $-CH_2CH_2OCH_3$; $R^3$ is hydrogen or methyl; and, $R^4$ is hydrogen, $-CH_2CH_2OCOCHCHCOOH$, $-CH_2CH_2OCOCH_2CH_2COOH$, or $-CH_2CH_2COOH$.

16 Claims, 9 Drawing Sheets

(56) References Cited

U.S. PATENT DOCUMENTS

| | | | |
|---|---|---|---|
| 2010/0304482 A1 | 12/2010 | Deshayes et al. | |
| 2010/0317113 A1 | 12/2010 | Deshayes et al. | |
| 2011/0104218 A1 | 5/2011 | Karles et al. | |
| 2011/0256117 A1 | 10/2011 | Yu et al. | |
| 2011/0256628 A1 | 10/2011 | Galperin et al. | |
| 2011/0275154 A1 | 11/2011 | Martin et al. | |
| 2012/0004339 A1 | 1/2012 | Chappa et al. | |
| 2012/0155438 A1 | 6/2012 | Shin et al. | |

FOREIGN PATENT DOCUMENTS

| | | |
|---|---|---|
| EP | 1 781 345 B1 | 1/2012 |
| KR | 10-2012-0070434 A | 6/2012 |
| WO | WO 02/072812 A2 | 9/2002 |
| WO | WO 2008/069761 A1 | 6/2008 |
| WO | WO 2009/099552 A2 | 8/2009 |
| WO | WO 2010/132636 A1 | 11/2010 |
| WO | WO 2010/138486 A1 | 12/2010 |
| WO | WO 2011/017050 A1 | 2/2011 |
| WO | WO 2011/106302 A1 | 9/2011 |

OTHER PUBLICATIONS

RPMI 1640 Media Formulation. Datasheet [online]. Life Technologies (Gibco), 2013 [retrieved on Jul. 29, 2013]. Retrieved from the Internet<URL: http://www.invitrogen.com/site/us/en/home/support/Product-Technical-Resources/media_formulation.114.html>.*

M199 Media Formulation. Datasheet [online]. Life Technologies (Gibco), 2013 [retrieved on Jul. 29, 2013]. Retrieved from the Internet<URL: http://www.invitrogen.com/site/us/en/home/support/Product-Technical-Resources/media_formulation.86.html>.* van Wachem et al., Adhesion of cultured human endothelial cells onto methacrylate polymers with varying surface wettability and charge. Biomaterials, vol. 8 (Sep. 1987) pp. 323-328.*

Altmann, et al., "Promotion of Osteoblast Differentiation in 3D Biomaterial Micro-Chip Arrays Comprising Fibronectin-Coated Poly(methyl methacrylate) Polycarbonate", Biomaterials, vol. 32, 2011, pp. 8947-8956.

Bural, et al., "Effect of Leaching Residual Methyl Methacrylate Concentrations on in vitro Cytotoxicity of Heat Polymerized Denture Base Acrylic Resin Processed with Different Polymerization Cycles", J Appl Oral Sci., pp. 306-312, 2010.

Dong, et al., "Thermoresponsive hyperbranched copolymer with multi acrylate functionality for in situ cross-linkable hyaluronic acid composite semi-IPN hydrogel", J Mater Sci: Mater Med, 2012, vol. 23, pp. 25-35

Ho, et al., "Creation of Biofunctionalized Micropatterns on Poly(methyl methacrylate) by Single-Step Phase Separation Method", ACS Publications, ACS Applied Materials & Interfaces, 2011, vol. 3, pp. 4496-4503.

Zhu, et al., "Encapsulating Hepatocytes with Chitosan in Physiological Conditions", pp. 1070-1074, Shen Wu Yi Xue Gong Cheng Xue Za Zhi Oct. 2006 vol. 23 No. 5.

Ormsby, et al., "Fatigue and biocompatibility properties of a poly(methyl methacrylate) bone cement with multi-walled carbon nanotubes", Acta Biomaterialia 8, 2012, pp. 1201-1212.

van Wachem, et al., "Adhesion of cultured human endothelial cells onto methacrylate polymers with varying surface wettability and charge", Biomaterials, vol. 8, Sep. 1987, pp. 323-328.

Veleva, et al., "Interactions Between Endothelial Cells and Electrospun Methacrylic Terpolymer Fibers for Engineered Vascular Replacements", Journal of Biochemical Materials Research Part A, 2009, pp. 1131-1139.

Villa-Diaz, et al., "Derivation of Mesenchymal Stem Cells from Human Induced Pluripotent Stem Cells Cultured on Synthetic Substrates", Stem Cells, 2012, vol. 30, pp. 1174-1181.

Yamada, et al., "Enhanced cell aggregation and liver functions using polymers modified with a cell-specific ligand in primary hepatocyte cultures", Journal of Bioscience and Bioengineering, vol. 88, No. 5, 1999, pp. 557-562.

Yang, et al., "In Situ Mineralization of Hydroxyapatite on Electrospun Chitosan-Based Nanofibrous Scaffolds", Macromolecular Bioscience, 2008, vol. 8, pp. 239-246.

Zhou, et al., "Photopolymerized Water-Soluble Chitosan-Based Hydrogel as Potential Use in Tissue Engineering", International Journal of Biological Macromolecules, vol. 48, 2011, pp. 408-413.

EPO Extended European Search Report for Appl. No. 12196546.1 dated Mar. 5, 2013.

* cited by examiner

CELL CULTURE SYSTEM AND SERUM-FREE METHOD FOR CULTIVATING CELLS

CROSS REFERENCE TO RELATED APPLICATIONS

This application is based upon and claims the benefit of priority from the prior Taiwan Patent Application No. 101141978, filed on Nov. 12, 2012, the entire contents of which are incorporated herein by reference.

TECHNICAL FIELD

The disclosure relates to a cell culture system and a serum-free method for cultivating cells.

BACKGROUND

For cultivating cells, in the past, a culture medium was supplemented with serum, which serves as a universal nutrient for the growth and maintenance of all mammalian cell lines that produce biologically active products. Although widely used, the serum has many limitations. It contains high levels of numerous proteins which interfere with the limited quantities of the desired protein of interest produced by the cells. The proteins derived from the serum must be separated from the product during downstream processing such as purification of the protein of interest, which complicates the process and increases the cost. Further, when culturing cells with the serum, a risk of causing infections exists, and the quality between batches is difficult to control. There is therefore a great demand for the development of alternative media free from animal serum for maintaining the growth of cells during the production of biologically active products.

A cell attachment factor (such as an extracellular matrix (ECM)) is used to coat on a substrate for cell culture for promoting the growth of cells, when the cells are cultivated with a serum-free medium. On the other hand, cells cultivated without the extracellular matrix are induced to undergo apoptosis. Generally, an extracellular matrix can include a glycosaminoglycan (GAG) or further include a fibrous protein (such as collagen, laminin, fibronectin, or elastin). For example, the serum-free medium StemPro MSC SFM (sold and manufactured by Invitrogen) has to be used with a petri dish coated with the extracellular matrix for cell culture. However, since the principal component of an extracellular matrix is protein which is generally obtained from organisms, the extracellular matrix has a high cost. Further, the quality of an extracellular matrix prepared and purified from human tissue or blood is unstable.

For the foregoing reasons, there is a need for new methods for promoting the growth of cells, especially when cultivated under serum-free and extracellular-matrix free conditions.

SUMMARY

An exemplary embodiment of the disclosure provides a cell culture system including: a substratum, wherein the substratum has a surface; and a polymer disposed on the surface. It should be noted that the polymer is prepared by polymerizing a first monomer with a second monomer, and the first monomer has a structure as represented by Formula (I), and the second monomer has a structure as represented by Formula (II):

Formula (I)

Formula (II)

wherein, $R^1$ is hydrogen or methyl; $R^2$ is methyl, ethyl, or —$CH_2CH_2OCH_3$; $R^3$ is hydrogen or methyl; and, $R^4$ is hydrogen, —$CH_2CH_2OCOCHCHCOOH$, —$CH_2CH_2OCOCH_2CH_2COOH$, or —$CH_2CH_2COOH$.

According to embodiments of the disclosure, the disclosure further provides a serum-free method for cultivating cells including: providing a substratum having a polymer; and applying a cell on a surface of the polymer for cultivating cells. Particularly, the polymer is prepared by polymerizing the first monomer with the second monomer, and the first monomer has a structure as represented by Formula (I), and the second monomer has a structure as represented by Formula (II):

Formula (I)

Formula (II)

wherein, $R^1$ is hydrogen or methyl; $R^2$ is methyl, ethyl, or —$CH_2CH_2OCH_3$; $R^3$ is hydrogen or methyl; and, $R^4$ is hydrogen, —$CH_2CH_2OCOCHCHCOOH$, —$CH_2CH_2OCOCH_2CH_2COOH$, or —$CH_2CH_2COOH$. It should be noted that the method for cultivating cells of the disclosure does not employ a serum or cell attachment factor.

A detailed description is given in the following embodiments with reference to the accompanying drawings.

DRAWINGS

The disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a cell culture system and a serum-free method for cultivating cells. The method for cultivating cells of the disclosure employs a specific polymer for promoting the growth of cells without a serum or cell attachment factor, resulting in reduced cost of cell cultures and more stable quality of cells.

Figure 1:
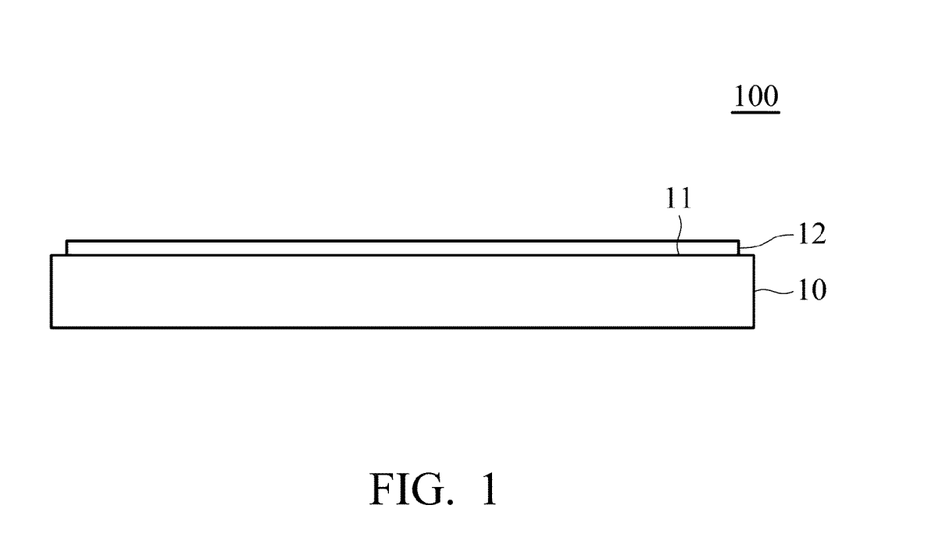
FIG. 1 is a cross-section showing a cell culture system according to an embodiment of the disclosure.

According to an embodiment of the disclosure, as shown in FIG. 1, the cell culture system 100 includes a substratum 10, wherein the substratum 10 has a surface 11. A polymer layer 12 is formed on the surface 11. It should be noted that, since the cell culture system of the disclosure includes a specific polymer layer 12 for promoting the growth of cells, the substratum 10 employed by the cell culture system of the disclosure is unlimited and can be a conventional substratum serving as a carrier for supporting the polymer layer 12. For example, the material of the substratum can be glass, ceramics, resin, plastic, or semiconductor material. The shape of the substratum is also unlimited. The accompanying drawings show the substratum 10 in a plain rectangle in order to simplify the illustration. Further, the surface 11 of the substratum 10 can be planar, curved, or combinations thereof, and can be smooth or rough. In an embodiment of the disclosure, the surface can be porous. The polymer layer 12 of the disclosure is made of a polymer, and the polymer is prepared by polymerizing the first monomer with the second monomer. Herein, the first monomer can have a structure as represented by Formula (I):

Formula (I)

wherein, $R^1$ is hydrogen, or methyl; $R^2$ is methyl, ethyl, or —$CH_2CH_2OCH_3$. For example, the first monomer can include methyl methacrylate (MMA), methoxy ethyl methacrylate (MEMA), methyl acrylate (MA), ethyl acrylate (EA), or combinations thereof. The second monomer can have a structure as represented by Formula (II):

Formula (II)

wherein, $R^3$ is hydrogen, or methyl; and $R^4$ is hydrogen, —$CH_2CH_2OCOCHCHCOOH$, —$CH_2CH_2OCOCH_2CH_2COOH$, or —$CH_2CH_2COOH$. For example, the second monomer can include methacrylic acid (MA-H), mono-2-(methacryloyloxy)ethyl succinate (MAES-H), 2-carboxy ethyl acrylate (CEA), mono-(2-acryloyloxyethyl) succinate (AES-H), acrylic acid (A-H), mono-2-(methacryloyloxy)ethyl maleate (MAEM-H), or combinations thereof. According to an embodiment of the disclosure, the molar ratio between the first monomer and the second monomer is between 1:9 and 9:1, such as between 1:9 and 8:2, between 1:9 and 7:3, between 2:8 and 9:1, between 3:7 and 9:1, or between 2:8 and 8:2. According to an embodiment of the disclosure, the polymer prepared by polymerizing the first monomer with the second monomer can have a weight averaged molecular weight of between 800,000 and 4,000,000, and the molecular weight dispersion index of the polymer is between 1 and 3.

For example, the method for preparing the polymer of the disclosure can include the following steps. The first monomer, the second monomer, the thermoinitiator (such as azobis (isobutyro)nitrile (AIBN)), and a solvent (such as dimethylformamide (DMF) or isopropyl alcohol (IPA)) are added to a reaction tube equipped with a stirrer bar. Next, the reaction tube is placed into a Radleys Carousel reactor, purged with nitrogen gas for 30 minutes and then sealed. After heating the Radleys Carousel reactor to 60° C., it is left to stir overnight. After allowing it to cool to room temperature, the result is subjected to a reprecipitiation into 150 ml solvent (such as deionized water, saturated salt solution or diethyl ether). The precipitate is then washed with solvent (such as deionized water or diethyl ether). The polymer is dried in a vacuum oven at 40° C.

The cell culture system of the disclosure includes a substratum, wherein the aforementioned polymer is disposed on a surface of the substratum (the polymer can be dissolved into a volatile solvent (such as THF)). The substratum surface can be optionally treated by a surface plasma in order to activate the surface and provide better adhesion of the deposited polymer layer (the plasma activation step is only necessary for specific polymers and given surfaces). The method for disposing the polymer on the surface of the substratum includes the following steps. First, a solution including the polymer is prepared by dissolving the polymer into a solvent. Next, the solution is dispensed on the surface of the substratum, left to react and subsequently either left to dry or excess solution can be removed. Further, the substratum with coated polymer layer can be baked at 40° C. to ensure removal of remaining solvents.

Standard methods may be used to prepare the polymers and coat them onto a substrate. For example, plasma polymerization and plasma induced graft polymerization can afford the direct formation of the polymer layer onto a substrate in a single step. Also some of these co-polymers may be prepared by the hydrolysis of bulk poly(methyl methacrylate), available commercially as Perspex.

According to another embodiment, the disclosure provides a serum-free method for cultivating cells. Namely, the disclosure provides a method for cultivating cells (such as adherent cells) with a cell culture medium which is free of a serum or cell attachment factor. For example, the serum-free method for cultivating a cell can include the following steps. First, a substratum having a polymer is provided. Next, a cell is applied to a surface of the polymer for cell culture. Further, a cell culture medium is provided during cell culture, wherein the cell culture medium is free of a serum or cell attachment factor. Particularly, the polymer is prepared by polymerizing the aforementioned first monomer with the aforementioned second monomer.

According to an embodiment of the disclosure, the cell used in the method of the disclosure can be an adherent cell, such as mesenchymal stem cells or dermal fibroblasts. The mesenchymal stem cell can be derived from various tissues or organs, such as bone marrow mesenchymal stem cells, adipose tissue-derived stem cells, or Wharton's jelly stem cells.

The conventional cell culture method employing a cell culture medium having a serum or cell attachment factor (such as extracellular matrix) has disadvantages in that there is a risk for causing infections and high costs, and it is difficult to control the quality between batches. The method employing the specific polymer for cultivating cells of the disclosure can promote the growth of cells with a cell culture medium free of a serum or cell attachment factor, and the polymer has a low production cost. Therefore, the disclosure provides a cell culture system and a cell culture method for replacing conventional cell culture methods employing the cell culture medium having a serum or cell attachment factor.

The following examples are intended to illustrate the disclosure more fully without limiting the scope of the disclosure, since numerous modifications and variations will be apparent to those skilled in this art.

Polymer Preparation

Table 1 discloses the compound structures, names and symbols for the compounds in the Preparation Examples of the disclosure for better understanding.

TABLE 1

| structure | name | symbol |
| --- | --- | --- |
| | methyl methacrylate | MMA |
| | methoxy ethyl methacrylate | MEMA |
| | methyl acrylate | MA |
| | ethyl acrylate | EA |
| | methacrylic acid | MA-H |
| | mono-2-(methacryloyloxy)ethyl succinate) | MAES-H |
| | 2-carboxy ethyl acrylate | CEA |
| | mono-(2-acryloyloxyethyl) succinate) | AES-H |
| | acrylic acid | A-H |

TABLE 1-continued

| structure | name | symbol |
|---|---|---|
| (structure shown) | mono-2-(methacryloyloxy)ethyl maleate) | MAEM-H |

PREPARATION EXAMPLE 1

First, the first monomer (MMA), second monomer (MAES-H), azobis(isobutyro)nitrile (AIBN), and dimethylformamide (DMF) were added into a reaction tube with a stirrer bar. Particularly, the molar ratio between the first monomer and the second monomer was 7:3. Next, the reaction tube was disposed into a Radleys Carousel reactor, purged with nitrogen gas for 30 min and then sealed. After heating the Radleys Carousel reactor to 60° C. and stirring overnight after cooling to room temperature, the result was subjected to a reprecipitation with 150 mL of deionized water, and then the precipitate thereof was washed with deionized water. After drying, the polymer (1) was obtained.

The number average molecular weight (Mn), weight averaged molecular weight (Mw), and molecular weight dispersion index (Mw/Mn) of the obtained polymer were measured by gel permeation chromatography (GPC) analysis, and the results are shown in Table 2.

PREPARATION EXAMPLES 2-30

Preparation Examples 2-30 were performed in the same manner as in Preparation Example 1 except that the first monomer, second monomer, and molar ratio between the first monomer and the second monomer shown in Table 2 were used instead of those in Preparation Example 1, obtaining the polymers (2)-(30).

Next, the number average molecular weight (Mn), weight averaged molecular weight (Mw), and molecular weight dispersion index (Mw/Mn) of the obtained polymers were measured by gel permeation chromatography (GPC) analysis, and the results are shown in Table 2.

TABLE 2

| | polymer preparation | | | measurement | | |
|---|---|---|---|---|---|---|
| | first monomer (M1) | second monomer (M2) | molar ratio between the first monomer and the second monomer (M1:M2) | number average molecular weight (Mn) | weight averaged molecular weight (Mw) | molecular weight dispersion index (Mw/Mn) |
| polymer (1) | MMA | MAES-H | 7:3 | 2507400 | 2891500 | 1.15 |
| polymer (2) | MMA | MAEM-H | 7:3 | 2132000 | 3609000 | 1.69 |
| polymer (3) | MMA | MAEM-H | 5:5 | 1664000 | 1923000 | 1.16 |
| polymer (4) | MMA | MAEM-H | 3:7 | 793600 | 1056000 | 1.33 |
| polymer (5) | MMA | MAEM-H | 1:9 | 2170000 | 2602000 | 1.20 |
| polymer (6) | MMA | MA-H | 7:3 | 1059000 | 1141000 | 1.08 |
| polymer (7) | MMA | MA-H | 6:4 | 1029000 | 1122000 | 1.09 |
| polymer (8) | MMA | MA-H | 5:5 | 1151000 | 1257000 | 1.09 |
| polymer (9) | MMA | MA-H | 4:6 | 1021000 | 1111000 | 1.09 |
| polymer (10) | MMA | MA-H | 3:7 | 1346000 | 1468000 | 1.09 |
| polymer (11) | MMA | MA-H | 1:9 | 1100000 | 1174000 | 1.07 |
| polymer (12) | MMA | CEA | 7:3 | 1211000 | 1359000 | 1.12 |
| polymer (13) | MMA | CEA | 5:5 | 1128000 | 1248000 | 1.11 |
| polymer (14) | MMA | A-H | 7:3 | 1072000 | 1192000 | 1.11 |
| polymer (15) | MMA | A-H | 5:5 | 1024000 | 1141000 | 1.11 |
| polymer (16) | MMA | A-H | 1:9 | 697900 | 835900 | 1.20 |
| polymer (17) | MMA | AES-H | 7:3 | 2620000 | 3159000 | 1.21 |
| polymer (18) | MMA | AES-H | 5:5 | 1200000 | 1416000 | 1.18 |
| polymer (19) | MMA | AES-H | 1:9 | 1065000 | 1207000 | 1.13 |
| polymer (20) | MEMA | AES-H | 9:1 | 945800 | 2780000 | 2.94 |
| polymer (21) | MEMA | AES-H | 7:3 | 1427000 | 1694000 | 1.19 |
| polymer (22) | MEMA | AES-H | 3:7 | 1330000 | 1538000 | 1.16 |
| polymer (23) | MEMA | AES-H | 1:9 | 1163000 | 1326000 | 1.14 |
| polymer (24) | MA | MA-H | 7:3 | 1552000 | 1750000 | 1.13 |
| polymer (25) | MA | MA-H | 5:5 | 1595000 | 1804000 | 1.13 |
| polymer (26) | MA | MA-H | 2:8 | 1743000 | 1932000 | 1.11 |
| polymer (27) | EA | CEA | 5:5 | 1555000 | 1779000 | 1.14 |
| polymer (28) | EA | CEA | 2:8 | 1584000 | 1781000 | 1.12 |
| polymer (29) | EA | MA-H | 5:5 | 1628000 | 1847000 | 1.14 |
| polymer (30) | EA | MA-H | 2:8 | 2070000 | 2262000 | 1.09 |

Cell Culture

EXAMPLE 1

First, the polymer (1) of Preparation Example 1 was dissolved into tetrahydrofuran (THF) to prepare a solution. Next, the solution was coated on a circular cover glass (having a diameter of 13 mm) by spin-coating at room temperature, with a dry air purge under vacuum, forming a polymer layer. Next, human bone marrow mesenchymal stem cells (BMSC) were seeded onto the polymer layer with a cellular density distribution of 3000 cells/cm$^2$, and a cell culture medium (sold and manufactured by BD Biosciences with the trade No. of BD Mosaic™ hMSC SF Medium) was used for cultivating cells.

After the cells were cultivated for three days, the numbers of cells was measured by an ADAM Cell Counter (sold and manufactured by Digital Bio) and compared with a control group (performed in the same manner as in Example 1 except that there was no polymer of the disclosure disposed on the cover glass), and the results are shown in Table 3.

EXAMPLES 2-61

Examples 2-61 were performed in the same manner as in Example 1 except that the polymer and the cells shown in Table 3 were used instead of those in Example 1. After the cells were cultivated for three days, the numbers of cells was measured by an ADAM Cell Counter (sold and manufactured by Digital Bio), and the results are shown in Table 3.

TABLE 3

| | polymer | cell | numbers of cells compared with control group thereof |
|---|---|---|---|
| Example 1 | polymer (1) | BMSC | increasing |
| Example 2 | polymer (3) | BMSC | increasing |
| Example 3 | polymer (3) | Wj Cell | increasing |
| Example 4 | polymer (3) | Fibroblast | increasing |
| Example 5 | polymer (4) | BMSC | increasing |
| Example 6 | polymer (4) | ADSC | increasing |
| Example 7 | polymer (4) | Wj Cell | increasing |
| Example 8 | polymer (4) | Fibroblast | increasing |
| Example 9 | polymer (5) | BMSC | increasing |
| Example 10 | polymer (5) | ADSC | increasing |
| Example 11 | polymer (5) | Wj Cell | increasing |
| Example 12 | polymer (5) | Fibroblast | increasing |
| Example 13 | polymer (6) | BMSC | increasing |
| Example 14 | polymer (6) | ADSC | increasing |
| Example 15 | polymer (7) | BMSC | increasing |
| Example 16 | polymer (7) | ADSC | increasing |
| Example 17 | polymer (8) | BMSC | increasing |
| Example 18 | polymer (8) | ADSC | increasing |
| Example 19 | polymer (9) | BMSC | increasing |
| Example 20 | polymer (9) | ADSC | increasing |
| Example 21 | polymer (10) | BMSC | increasing |
| Example 22 | polymer (10) | ADSC | increasing |
| Example 23 | polymer (11) | BMSC | increasing |
| Example 24 | polymer (11) | ADSC | increasing |
| Example 25 | polymer (12) | BMSC | increasing |
| Example 26 | polymer (12) | ADSC | increasing |
| Example 27 | polymer (12) | Wj Cell | increasing |
| Example 28 | polymer (13) | ADSC | increasing |
| Example 29 | polymer (13) | Fibroblast | increasing |
| Example 30 | polymer (14) | BMSC | increasing |
| Example 31 | polymer (14) | ADSC | increasing |
| Example 32 | polymer (15) | BMSC | increasing |
| Example 33 | polymer (15) | ADSC | increasing |
| Example 34 | polymer (16) | BMSC | increasing |
| Example 35 | polymer (16) | ADSC | increasing |
| Example 36 | polymer (16) | Wj Cell | increasing |

TABLE 3-continued

| | polymer | cell | numbers of cells compared with control group thereof |
|---|---|---|---|
| Example 37 | polymer (16) | Fibroblast | increasing |
| Example 38 | polymer (17) | ADSC | increasing |
| Example 39 | polymer (18) | BMSC | increasing |
| Example 40 | polymer (18) | ADSC | increasing |
| Example 41 | polymer (19) | BMSC | increasing |
| Example 42 | polymer (19) | ADSC | increasing |
| Example 43 | polymer (21) | BMSC | increasing |
| Example 44 | polymer (21) | ADSC | increasing |
| Example 45 | polymer (22) | BMSC | increasing |
| Example 46 | polymer (22) | ADSC | increasing |
| Example 47 | polymer (24) | BMSC | increasing |
| Example 48 | polymer (25) | BMSC | increasing |
| Example 49 | polymer (25) | ADSC | increasing |
| Example 50 | polymer (25) | Fibroblast | increasing |
| Example 51 | polymer (26) | BMSC | increasing |
| Example 52 | polymer (26) | ADSC | increasing |
| Example 53 | polymer (26) | Fibroblast | increasing |
| Example 54 | polymer (27) | BMSC | increasing |
| Example 55 | polymer (27) | ADSC | increasing |
| Example 56 | polymer (28) | BMSC | increasing |
| Example 57 | polymer (28) | ADSC | increasing |
| Example 58 | polymer (29) | BMSC | increasing |
| Example 59 | polymer (29) | ADSC | increasing |
| Example 60 | polymer (30) | ADSC | increasing |
| Example 61 | polymer (30) | Wj Cell | increasing |

(remark: BMSC: human bone marrow mesenchymal stem cell; ADSC: human adipose tissue derived stem cell; Wj cells: human umbilical cord Wharton's jelly stem cell; and Fibroblast: human foreskin fibroblasts (Hs68))

Figure 2A:
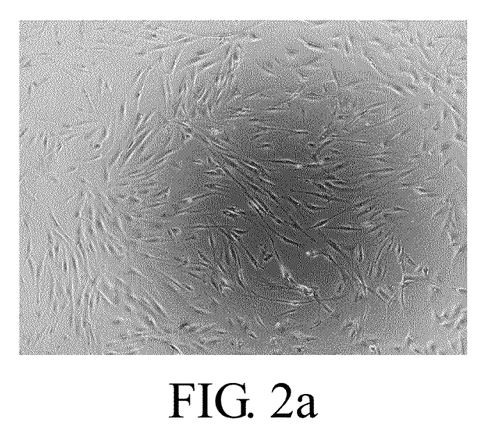
FIGS. 2a-2c respectively show photographs taken by a microscope of the cell culture systems of Examples 51 and 58 and the control group thereof after the cells were cultivated for three days.
Figure 2B:
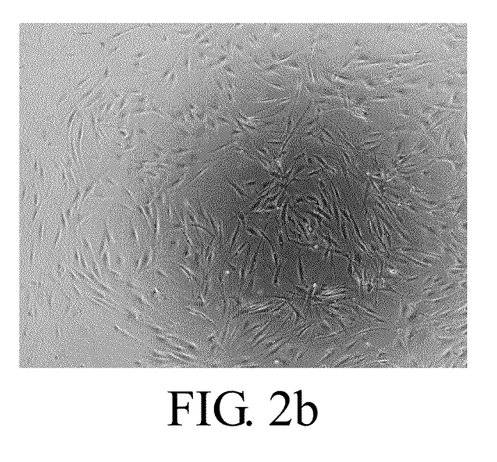
Figure 2C:
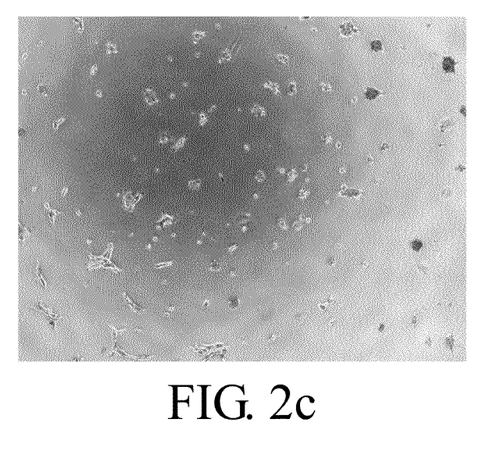

FIGS. 2a, and 2b respectively show photographs (taken by a microscope at a magnification of 40 times) of the cell (BMSC) culture systems of Examples 51 and 58 after the cells were cultivated for three days. Further, FIG. 2c shows photographs (taken by a microscope at a magnification of 40 times) of the cell (BMSC) culture systems of the control group of Examples 51 and 58 after the cells were cultivated for three days. As shown in FIGS. 2a and 2b, the cell culture system of Examples 51 and 58 promoted the growth of cells (the number of the cells increased). To the contrary, the number of the cells in the cell culture system of the control group was reduced and underwent apoptosis, as shown in FIG. 2c.

Figure 3A:
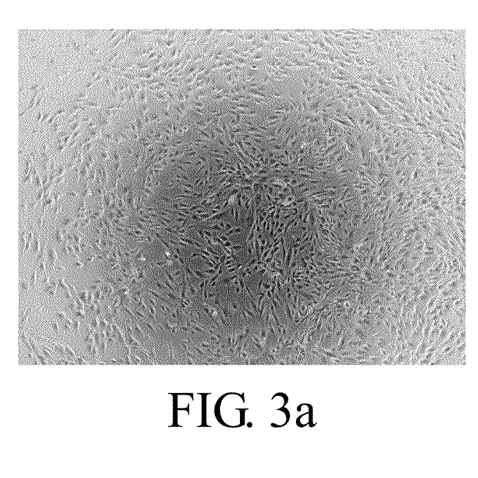
FIGS. 3a-3g respectively show photographs taken by a microscope of the cell culture systems of Examples 14, 16, 18, 20, 22, and 24 and the control group thereof after the cells were cultivated for three days.
Figure 3B:
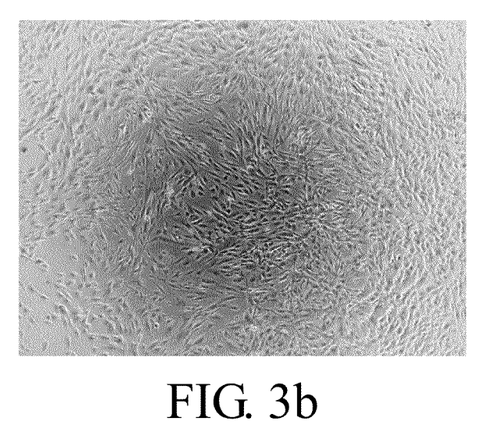
Figure 3C:
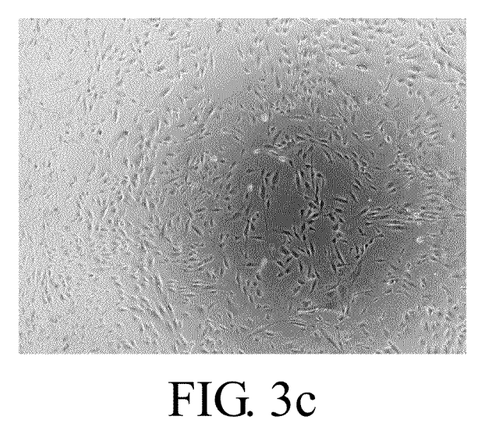
Figure 3D:
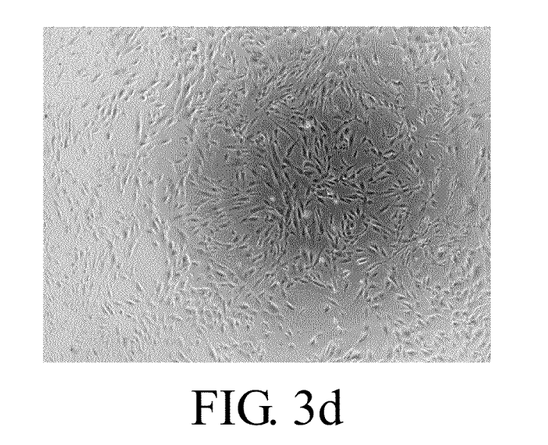
Figure 3E:
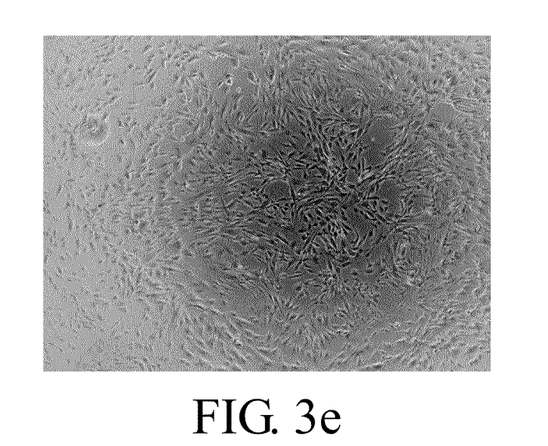
Figure 3F:
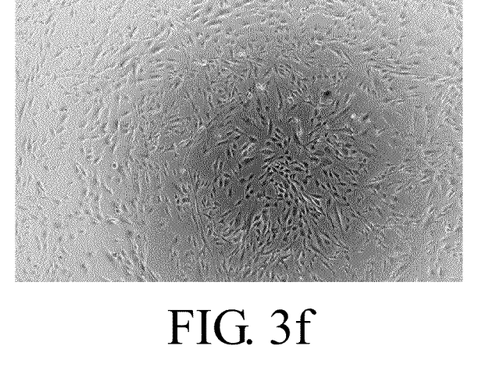
Figure 3G:
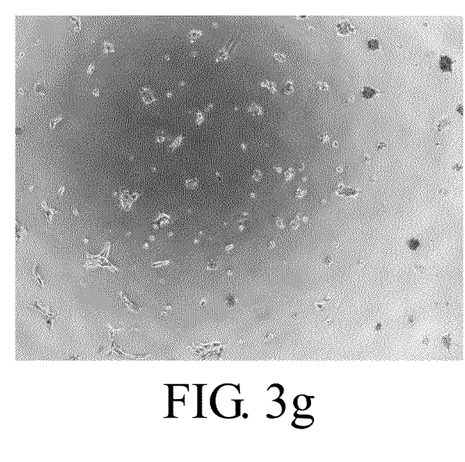

FIGS. 3a-3f respectively show photographs (taken by a microscope at a magnification of 40 times) of the cell (ADSC) culture systems of Examples 14, 16, 18, 20, 22, and 24 (having the same polymer (prepared from MMA and MA-H with various MMA/MA-H molar ratio) after the cells were cultivated for three days. Further, FIG. 3g shows photographs (taken by a microscope at a magnification of 40 times) of the cell (ADSC) culture systems of the control group of Examples 14, 16, 18, 20, 22, and 24 after the cells were cultivated for three days. As shown in FIGS. 3a-3f, the cell culture system of Examples 14, 16, 18, 20, 22, and 24 promoted the growth of cells (the number of the cells increased). To the contrary, the number of the cells in the cell culture system of the control group was reduced and underwent apoptosis, as shown in FIG. 3g.

EXAMPLE 62

First, the polymer (1) of Preparation Example 1 was dissolved into tetrahydrofuran (THF) to prepare a solution. Next, the solution was coated on a circular cover glass (having a diameter of 13 mm) by spin-coating at room temperature with a dry air purge under vacuum, forming a polymer layer. Next, human bone marrow mesenchymal stem cells (BMSC) were seeded to the polymer layer with a cellular density distribution of 3000 cells/cm$^2$, and a cell culture medium (sold and manufactured by Stem Cell Technologies with the trade No. of MesenCult-XF Basal Medium) was used for cultivating cells.

After the cells were cultivated for three days, the numbers of cells was measured by an ADAM Cell Counter (sold and manufactured by Digital Bio) and compared with a control group (performed in the same manner as in Example 62 except that there was no polymer of the disclosure disposed on the cover glass), and the results are shown in Table 4.

EXAMPLE 63-85

Examples 63-85 were performed in the same manner as in Example 62 except that the polymer and the cells shown in Table 4 were used instead of those in Example 62. After the cells were cultivated for three days, the numbers of cells was measured by an ADAM Cell Counter (sold and manufactured by Digital Bio), and the results are shown in Table 4.

TABLE 4

|  | polymer | cell | numbers of cells compared with control group thereof |
| --- | --- | --- | --- |
| Example 62 | polymer (1) | BMSC | increasing |
| Example 63 | polymer (1) | ADSC | increasing |
| Example 64 | polymer (1) | Wj Cell | increasing |
| Example 65 | polymer (3) | ADSC | increasing |
| Example 66 | polymer (3) | Wj Cell | increasing |
| Example 67 | polymer (3) | Fibroblast | increasing |
| Example 68 | polymer (4) | ADSC | increasing |
| Example 69 | polymer (4) | Wj Cell | increasing |
| Example 70 | polymer (4) | Fibroblast | increasing |
| Example 71 | polymer (5) | ADSC | increasing |
| Example 72 | polymer (5) | Fibroblast | increasing |
| Example 73 | polymer (6) | BMSC | increasing |
| Example 74 | polymer (6) | ADSC | increasing |
| Example 75 | polymer (7) | BMSC | increasing |
| Example 76 | polymer (7) | ADSC | increasing |
| Example 77 | polymer (7) | Wj Cell | increasing |
| Example 78 | polymer (8) | BMSC | increasing |
| Example 79 | polymer (8) | ADSC | increasing |
| Example 80 | polymer (8) | Wj Cell | increasing |
| Example 81 | polymer (12) | ADSC | increasing |
| Example 82 | polymer (12) | Wj Cell | increasing |
| Example 83 | polymer (18) | Wj Cell | increasing |
| Example 84 | polymer (19) | Fibroblast | increasing |
| Example 85 | polymer (23) | Wj Cell | increasing |

Figure 4A:
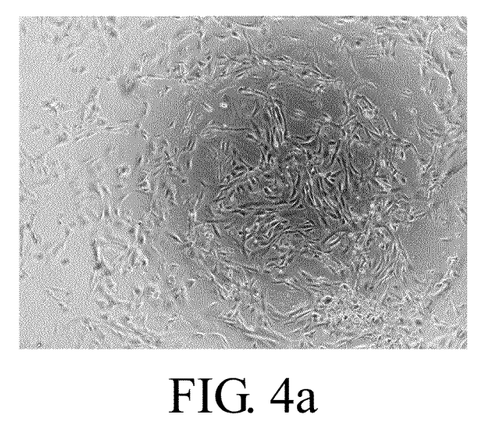
FIGS. 4a-4c respectively show photographs taken by a microscope of the cell culture systems of Examples 67 and 70 and the control group thereof after the cells were cultivated for three days.
Figure 4B:
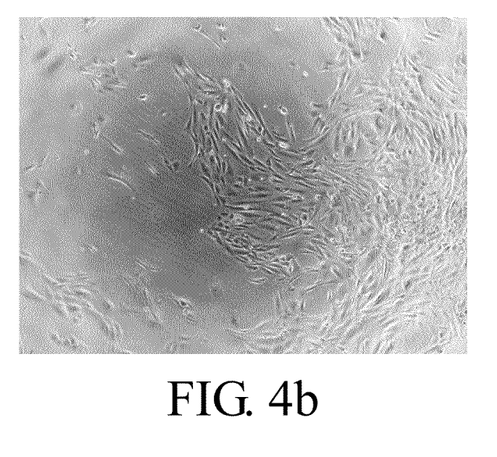
Figure 4C:
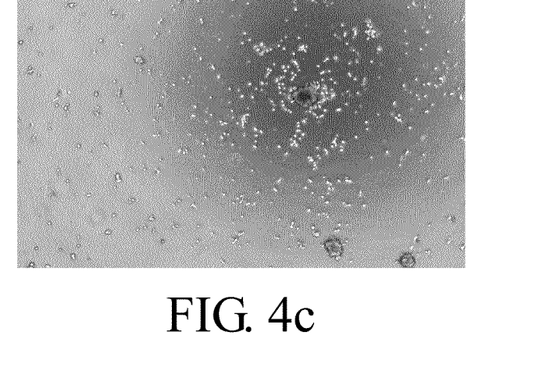

FIGS. 4a and 4b respectively show photographs (taken by a microscope at a magnification of 40 times) of the cell (Fibroblast) culture systems of Examples 67 and 70 after the cells were cultivated for three days. Further, FIG. 4c shows photographs (taken by a microscope at a magnification of 40 times) of the cell (Fibroblast) culture systems of the control group of Examples 67 and 70 after the cells were cultivated for three days. As shown in FIGS. 4a and 4b, the cell culture system of Examples 67 and 70 promoted the growth of cells (the number of the cells increased). To the contrary, the number of the cells in the cell culture system of the control group was reduced and underwent apoptosis, as shown in FIG. 4c.

EXAMPLE 86

First, the polymer (2) of Preparation Example 2 was dissolved into tetrahydrofuran (THF) to prepare a solution. Next, the solution was coated on a circular cover glass (having a diameter of 13 mm) by spin-coating at room temperature, with a dry air purge under vacuum, forming a polymer layer. Next, human adipose tissue derived stem cells (ADSC) were seeded onto the polymer layer with a cellular density distribution of 3000 cells/cm$^2$, and a cell culture medium (sold and manufactured by Invitrogen with the trade No. of StemPro MSC SFM Basal Medium) was used for cultivating cells.

After the cells were cultivated for three days, the numbers of cells was measured by an ADAM Cell Counter (sold and manufactured by Digital Bio) and compared with a control group (performed in the same manner as in Example 86 except that there was no polymer of the disclosure disposed on the cover glass), and the results are shown in Table 5.

EXAMPLES 87-102

Examples 87-102 were performed in the same manner as in Example 86 except that the polymer and the cells shown in Table 5 were used instead of those in Example 86. After the cells were cultivated for three days, the numbers of cells was measured by an ADAM Cell Counter (sold and manufactured by Digital Bio), and the results are shown in Table 5.

TABLE 5

|  | polymer | cell | numbers of cells compared with control group thereof |
| --- | --- | --- | --- |
| Example 86 | polymer (2) | ADSC | increasing |
| Example 87 | polymer (3) | BMSC | increasing |
| Example 88 | polymer (3) | Wj Cell | increasing |
| Example 89 | polymer (3) | Fibroblast | increasing |
| Example 90 | polymer (5) | BMSC | increasing |
| Example 91 | polymer (5) | ADSC | increasing |
| Example 92 | polymer (5) | Wj Cell | increasing |
| Example 93 | polymer (5) | Fibroblast | increasing |
| Example 94 | polymer (6) | Wj Cell | increasing |
| Example 95 | polymer (8) | Wj Cell | increasing |
| Example 96 | polymer (11) | BMSC | increasing |
| Example 97 | polymer (12) | Wj Cell | increasing |
| Example 98 | polymer (13) | Wj Cell | increasing |
| Example 99 | polymer (14) | Wj Cell | increasing |
| Example 100 | polymer (15) | Wj Cell | increasing |
| Example 101 | polymer (20) | Wj Cell | increasing |
| Example 102 | polymer (20) | Fibroblast | increasing |

Figure 5A:
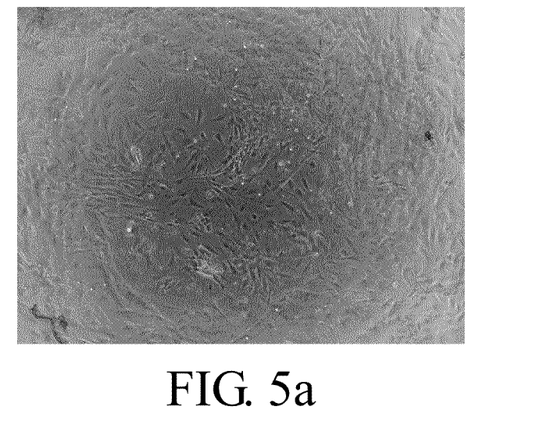
FIGS. 5a-5c respectively show photographs taken by a microscope of the cell culture systems of Examples 99 and 101 and the control group thereof after the cells were cultivated for three days.
Figure 5B:
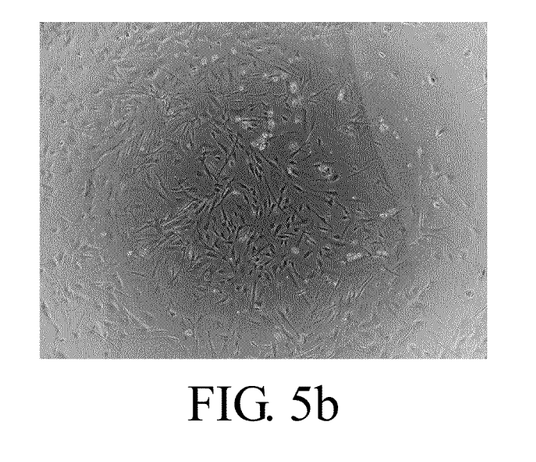
Figure 5C:
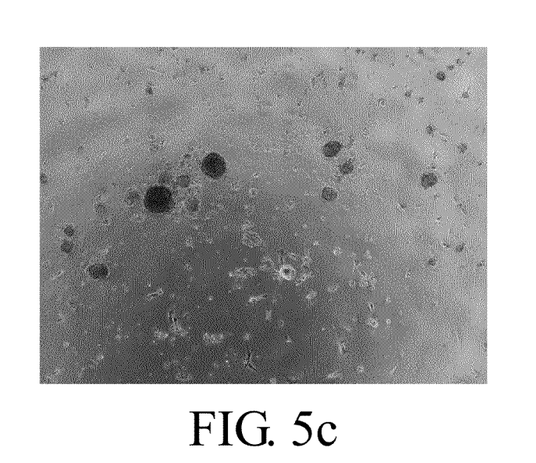

FIGS. 5a and 5b respectively show photographs (taken by a microscope at a magnification of 40 times) of the cell (Wj Cell) culture systems of Examples 99 and 101 after the cells were cultivated for three days. Further, FIG. 5c shows photographs (taken by a microscope at a magnification of 40 times) of the cell (Wj Cell) culture systems of the control group of Examples 99 and 101 after the cells were cultivated for three days. As shown in FIGS. 5a and 5b, the cell culture system of Examples 99 and 101 promoted the growth of cells (the number of the cells increased). To the contrary, the number of the cells in the cell culture system of the control group was reduced and underwent apoptosis, as shown in FIG. 5c.

As shown in Tables 3-5, due to the specific polymers disposed on the substratum, the cell culture system and the method for cultivating cells of the disclosure promoted the growth of cells, reduced the cost of cell cultures, and resulted in a more stable quality, under the condition where there were no serum or cell attachment factor used during cell culture.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A cell culture system, comprising:
a substratum, wherein the substratum has a surface; and
a polymer, disposed on the surface of the substratum, wherein the polymer is prepared by polymerizing a first monomer with a second monomer, and the first monomer has a structure as represented by Formula (I), and the second monomer has a structure as represented by Formula (II):

Formula (I)

Formula (II)

wherein, $R^1$ is hydrogen or methyl; $R^2$ is methyl, ethyl, or —CH$_2$CH$_2$OCH$_3$; $R^3$ is hydrogen or methyl; and, $R^4$ is hydrogen, —CH$_2$CH$_2$OCOCHCHCOOH, —CH$_2$CH$_2$OCOCH$_2$CH$_2$COOH, or —CH$_2$CH$_2$COOH, wherein $R^4$ is not hydrogen when $R^1$, $R^2$, and $R^3$ are methyl, and
wherein the polymer is not branched or cross-linked.

2. The cell culture system as claimed in claim 1, wherein the molar ratio between the first monomer and the second monomer is between 1:9 to 9:1.

3. The cell culture system as claimed in claim 1, wherein the first monomer comprises methyl methacrylate, methoxy ethyl methacrylate, methyl acrylate, ethyl acrylate, or combinations thereof.

4. The cell culture system as claimed in claim 1, wherein the second monomer comprises methacrylic acid, mono-2-(methacryloyloxy)ethyl succinate, 2-carboxy ethyl acrylate, mono-(2-acryloyloxyethyl) succinate, acrylic acid, mono-2-(methacryloyloxy)ethyl maleate, or combinations thereof.

5. The cell culture system as claimed in claim 1, wherein the first monomer comprises methyl methacrylate, when the second monomer comprises mono-2-(methacryloyloxy)ethyl maleate), 2-carboxy ethyl acrylate, acrylic acid, or mono-(2-acryloyloxyethyl) succinate).

6. The cell culture system as claimed in claim 1, wherein the second monomer comprises methacrylic acid, when the first monomer comprises methyl acrylate, or ethyl acrylate.

7. A serum-free method for cultivating cells, comprising:
providing a substratum having a polymer, wherein the polymer is prepared by polymerizing a first monomer with a second monomer, and the first monomer has a structure as represented by Formula (I), and the second monomer has a structure as represented by Formula (II):

Formula (I)

Formula (II)

wherein, $R^1$ is hydrogen or methyl; $R^2$ is methyl, ethyl, or —CH$_2$CH$_2$OCH$_3$; $R^3$ is hydrogen or methyl; and, $R^4$ is hydrogen, —CH$_2$CH$_2$OCOCHCHCOOH, —CH$_2$CH$_2$OCOCH$_2$CH$_2$COOH, or —CH$_2$CH$_2$COOH; and
applying a cell to a surface of the polymer for cell culture, wherein $R^4$ is not hydrogen when $R^1$, $R^2$, and $R^3$ are methyl, and
wherein the polymer is not branched or cross-linked.

8. The serum-free method for cultivating cells as claimed in claim 7, wherein the cell is an adherent cell.

9. The serum-free method for cultivating cells as claimed in claim 8, wherein the adherent cell is a mesenchymal stem cell, or dermal fibroblast.

10. The serum-free method for cultivating cells as claimed in claim 7, further comprising:
providing a cell culture medium to the substratum, wherein the cell culture medium is free of a serum or cell attachment factor.

11. The serum-free method for cultivating cells as claimed in claim 10, wherein the cell attachment factor is an extracellular matrix.

12. The serum-free method for cultivating cells as claimed in claim 7, wherein the molar ratio between the first monomer and the second monomer is between 1:9 to 9:1.

13. The serum-free method for cultivating cells as claimed in claim 7, wherein the first monomer comprises methyl methacrylate, methoxy ethyl methacrylate, methyl acrylate, ethyl acrylate, or combinations thereof.

14. The serum-free method for cultivating cells as claimed in claim 7, wherein the second monomer comprises methacrylic acid, mono-2-(methacryloyloxy)ethyl succinate, 2-carboxy ethyl acrylate, mono-(2-acryloyloxyethyl) succinate, acrylic acid, mono-2-(methacryloyloxy)ethyl maleate, or combinations thereof.

15. The serum-free method for cultivating cells as claimed in claim 7, wherein the first monomer comprises methyl methacrylate, when the second monomer comprises mono-2-(methacryloyloxy)ethyl maleate), 2-carboxy ethyl acrylate, acrylic acid, or mono-(2-acryloyloxyethyl) succinate).

16. The serum-free method for cultivating cells as claimed in claim 7, wherein the second monomer comprises methacrylic acid, when the first monomer comprises methyl acrylate, or ethyl acrylate.

* * * * *